United States Patent
Matsubara et al.

[11] Patent Number: 5,993,624
[45] Date of Patent: Nov. 30, 1999

[54] CARBON DIOXIDE GAS SENSOR

[75] Inventors: Shogo Matsubara, Kasuga; Shoichi Shimizu, Fukuoka; Shinji Morimoto, Onojo; Shinichiro Kaneko, Fukuoka, all of Japan

[73] Assignee: Matsushita Electric Industrial Co., Ltd., Osaka, Japan

[21] Appl. No.: 08/759,872

[22] Filed: Dec. 3, 1996

[30] Foreign Application Priority Data

Dec. 7, 1995 [JP] Japan .................... 7-318738
Mar. 27, 1996 [JP] Japan .................... 8-072722
Aug. 30, 1996 [JP] Japan .................... 8-230023

[51] Int. Cl.$^6$ .................... G01N 27/02; G01N 27/407
[52] U.S. Cl. .................... 204/424; 204/421; 204/426; 205/784; 264/109; 264/603; 422/98
[58] Field of Search .................... 204/421–429; 205/783.5, 784, 784.5, 785; 422/98

[56] References Cited

U.S. PATENT DOCUMENTS

| | | | |
|---|---|---|---|
| 4,321,577 | 3/1982 | Carlson | 422/98 |
| 4,574,264 | 3/1986 | Takahashi et al. | 422/98 |
| 4,715,944 | 12/1987 | Yanagida et al. | 204/426 |
| 4,755,473 | 7/1988 | Nishio et al. | 422/98 |
| 5,194,134 | 3/1993 | Futata et al. | 204/426 |

FOREIGN PATENT DOCUMENTS

| | | |
|---|---|---|
| 424548 | 1/1992 | Japan . |
| 627071 | 2/1994 | Japan . |

*Primary Examiner*—T. Tung
*Attorney, Agent, or Firm*—Stevens, Davis, Miller & Mosher

[57] ABSTRACT

A carbon dioxide gas sensor for detecting carbon dioxide gas concentration wherein the carbon dioxide gas detection part consists essentially of a carbonate, a carbonate decomposition catalyst and a semiconductor oxide, particularly preferably $BaCO_3$, $CeO_2$ and $CuO$ mixed in a specific molar ratio.

A process for producing the carbon dioxide detection part of a carbon dioxide gas sensor, wherein the raw-materials in the form of acetic acid salts are uniformly dissolved in a solvent, then dried and ground to produce a ceramic material with a small average particle diameter.

20 Claims, 3 Drawing Sheets

CARBON DIOXIDE GAS SENSOR

BACKGROUND OF THE INVENTION

The present invention relates to a carbon dioxide gas sensor for measuring and controlling carbon dioxide gas concentration which is used in monitors for monitoring pollution of the air in living spaces, such as inside a room and inside a vehicle, monitors for controlling air conditioning systems, monitors for managing disaster prevention, monitors for controlling carbon dioxide gas concentration during the transportation and storage of perishable foods, and carbon dioxide gas concentration monitoring system in biotechnical facilities and horticulture under structure, to a process for producing the sensor, and to a carbon dioxide gas sensor device.

Previously known carbon dioxide gas sensors employed for these uses include those of infrared absorption type, electromotive force detection type and capacitance detection type.

An infrared absorption type carbon dioxide gas sensor consists essentially of a light emitting element which emits laser light and a light receiving element sensor which receives the laser light emitted from the light emitting element and measures its intensity. Its working principle lies in receiving the laser light whose intensity has been changed by the presence of carbon dioxide gas and measuring the intensity of the light with the light receiving element sensor, and thereby detecting the carbon dioxide gas concentration. However, though the principle makes use of the fact that carbon dioxide gas absorbs a light of specific wavelength, the light of this wavelength is also absorbed by water, so that the measuring accuracy is adversely influenced by the presence of moisture. Thus, an infrared absorption type carbon dioxide gas sensor, in principle, is capable of accurate determination of carbon dioxide gas concentration if moisture is eliminated; but apparatuses which use this sensor inevitably have a large size and complicated structure owing to the necessity of eliminating moisture, and hence have problems in productivity, mass productivity and production cost, so that the use of sensors of this type has been limited to such special fields as in analytical instruments.

An electromotive force detection type carbon dioxide gas sensor consists essentially of such a solid electrolyte material as NASICON (Na Super Ionic Conductor) and Li-Ti-oxide, and a secondary electrode material comprising alkali metal carbonates, such as $Li_2CO_3$ and $Na_2CO_3$. In this sensor, alkali metal ions formed by the decomposition of the alkali metal carbonate in the secondary electrode transfer through the solid electrolyte to generate an electromotive force corresponding to carbon dioxide gas concentration. However, NASICON of the solid electrolyte material and the alkali metal carbonate of the main component of the secondary electrode material are liable to dissolve in water. Accordingly, the sensor of this type has problems in that, when used in an environment of high humidity, it shows low reliability and short life due to deterioration of characteristic properties caused by swelling, development of peeling of the electrode, or dissolving out of the alkali metal carbonate.

The above-mentioned problems are overcome to some extent in a capacitance detection type carbon dioxide gas sensor. This sensor makes use of a reversible carbonate-forming reaction between a non-compound type metal oxide and carbon dioxide gas to change its electric property, such as capacitance or impedance and thereby to detect the carbon dioxide gas concentration.

JP-A-4-24548 discloses carbon dioxide gas sensors which detect carbon dioxide gas concentration by changing the capacitance of a mixture of a non-compound type metal oxide, such as CuO and NiO, and a perovskite type oxide, such as $BaTiO_3$ and $SrTiO_3$.

These sensors are prepared by using a commercially available material, such as CuO and $BaTiO_3$, or a material prepared by mixing the commercially available materials and then heat-treating the mixture. The materials used are mixed so as to give a predetermined mixing ratio, then pulverized, shaped and heat-treated to give a plate-formed carbon dioxide gas detection past main body. Thereafter, an electrode part for taking out electric signals is provided to measure the change of such electric properties as capacitance or impedance, thus to complete a carbon dioxide gas sensor.

However, the capacitance detection type carbon dioxide gas sensors as mentioned above which comprise a mixture of a non-compound type metal oxide and a perovskite type oxide or a mixture of an insulating oxide and an oxide which forms a carbonate at high temperature have problems of a low detection sensitivity to carbon dioxide gas and a low speed of response. Moreover, they are still unsatisfactory in moisture resistance and in reliability, for example, they show an insufficient life in long-term operation.

Furthermore, in the capacitance detection type carbon dioxide gas sensor, the necessary change in electric properties is obtained, as mentioned above, by a reversible carbonate-forming reaction between the non-compound type metal oxide and carbon dioxide gas, so that the sensor needs to be heated all the time at a temperature of 400–600° C. Therefore, in a capacitance detection type carbon dioxide gas sensor, which has a heating means as one of the essential constituents, a structure of carbon dioxide gas sensor device which is as small-sized as possible and yet has a good heat efficiency is eagerly desired in order to attain the protection of electric circuits and energy-saving of the heating means itself.

SUMMARY OF THE INVENTION

One object of the present invention is to provide, overcoming the above-mentioned problems, a capacitance detection type carbon dioxide gas sensor which has an improved detection sensitivity to carbon dioxide gas, an increased speed of response, an increased life in long-term operation and an improved reliability in high humidity environment, and a process for producing the sensor.

The other object of the present invention is to provide a capacitance detection type carbon dioxide gas sensor device which can be used in many variety of uses by disclosing a structure of a carbon dioxide gas sensor device which is small in size and has a good heat efficiency.

DETAILED DESCRIPTION OF THE INVENTION

Some embodiments of the present invention are described below with reference to FIGS. 1–3.

Figure 1:
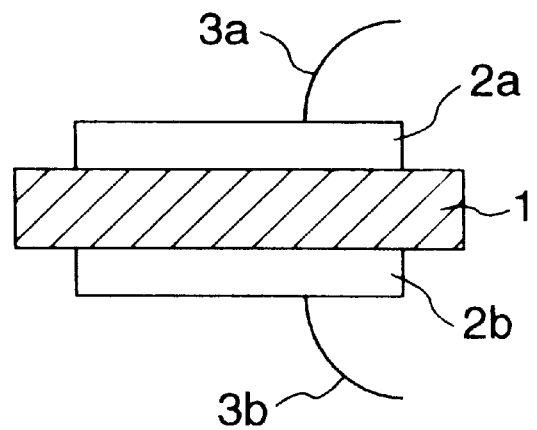
FIG. 1 is a sectional view of a carbon dioxide gas sensor in the first embodiment of the present invention.

FIG. 1 is a sectional view of a carbon dioxide gas sensor in the first embodiment of the present invention.

The carbon dioxide gas sensor in the present embodiment comprises a carbon dioxide gas detection part 1, electricity-conducting electrodes 2a and 2b provided on the carbon dioxide gas detection part 1, and lead wires 3a and 3b provided on the electricity-conducting electrodes 2a and 2b.

The carbon dioxide gas detection part 1 is prepared by a mixture which comprises at least one carbonate and at least one carbonate decomposition catalyst, preferably comprises a mixture of at least one carbonate, at least one carbonate decomposition catalyst and at least one semiconductor oxide.

Preferably, the carbonate is selected from the group consisting of alkali metal carbonates and alkaline earth metal carbonates. Examples of the carbonate are such as $BaCO_3$, $CaCo_3$, $SrCO_3$, $Li_2CO_3$. Among these examples $BaCO_3$ is preferred.

Preferably, the carbonate decomposition catalyst is selected from the group consisting perovskite type oxides and rare earth element oxides. Examples of the carbonate decomposition catalyst are such as $CeO_2$, $BaTiO_3$, $SrTiO_3$, $CaTiO_3$, $BaCeO_3$, $SrCeO_3$, $Y_2O_3$, $Gd_2O_3$, $La_2O_3$, $Sc_2O_3$. Among these examples $CeO_2$ is preferred.

Examples of the semiconductor oxide are such as copper oxides, lead oxides, iron oxides, zinc oxides, tin oxides.

The molar mixing ratio of the carbonate, the carbonate decomposition catalyst and the semiconductor oxide, expressed as the carbonate: the carbonate decomposition catalyst: the semiconductor oxide=X:Y:Z (X+Y+Z=100), X, Y and Z respectively fall within the range defined by the equation $3 \leq X \leq 50$, $30 \leq Y \leq 80$ and $0 \leq Z \leq 45$.

The electricity-conducting electrodes 2a and 2b are prepared by a material which has a low electric resistance at an operating temperature of 400–600° C. and undergoes substantially no change with the lapse of time. For example, the electrodes can be formed by screen-printing a paste containing any of noble metals and oxides conductors preferably Au, Pt, Ag, $RuO_2$, more preferably Pt, followed by heat treatment. As the lead wires 3a and 3b, Pt, Ni, Au or the like in the form of plate or wire is used.

Figure 2:
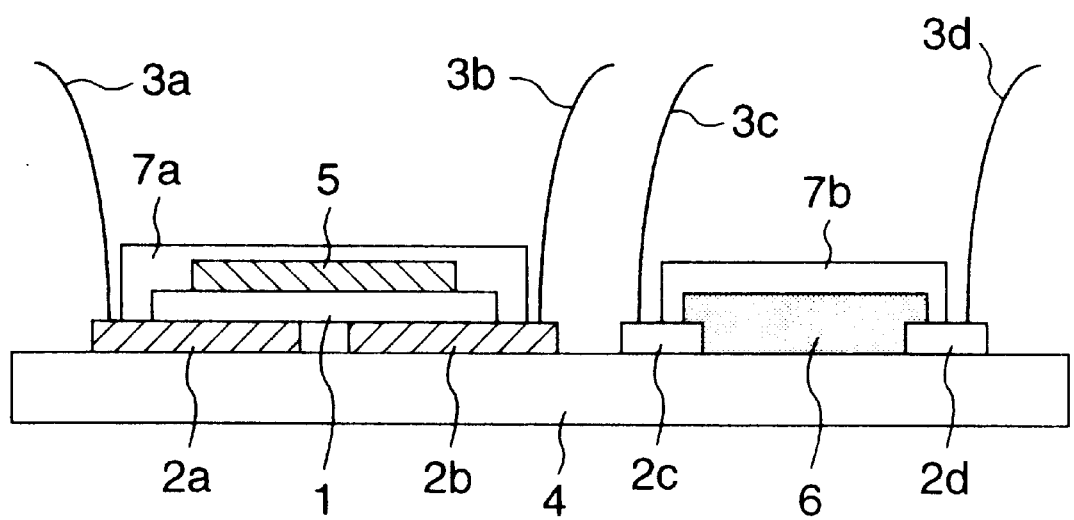
FIG. 2 is a sectional view of a carbon dioxide gas sensor in the second embodiment of the invention.
Figure 3:
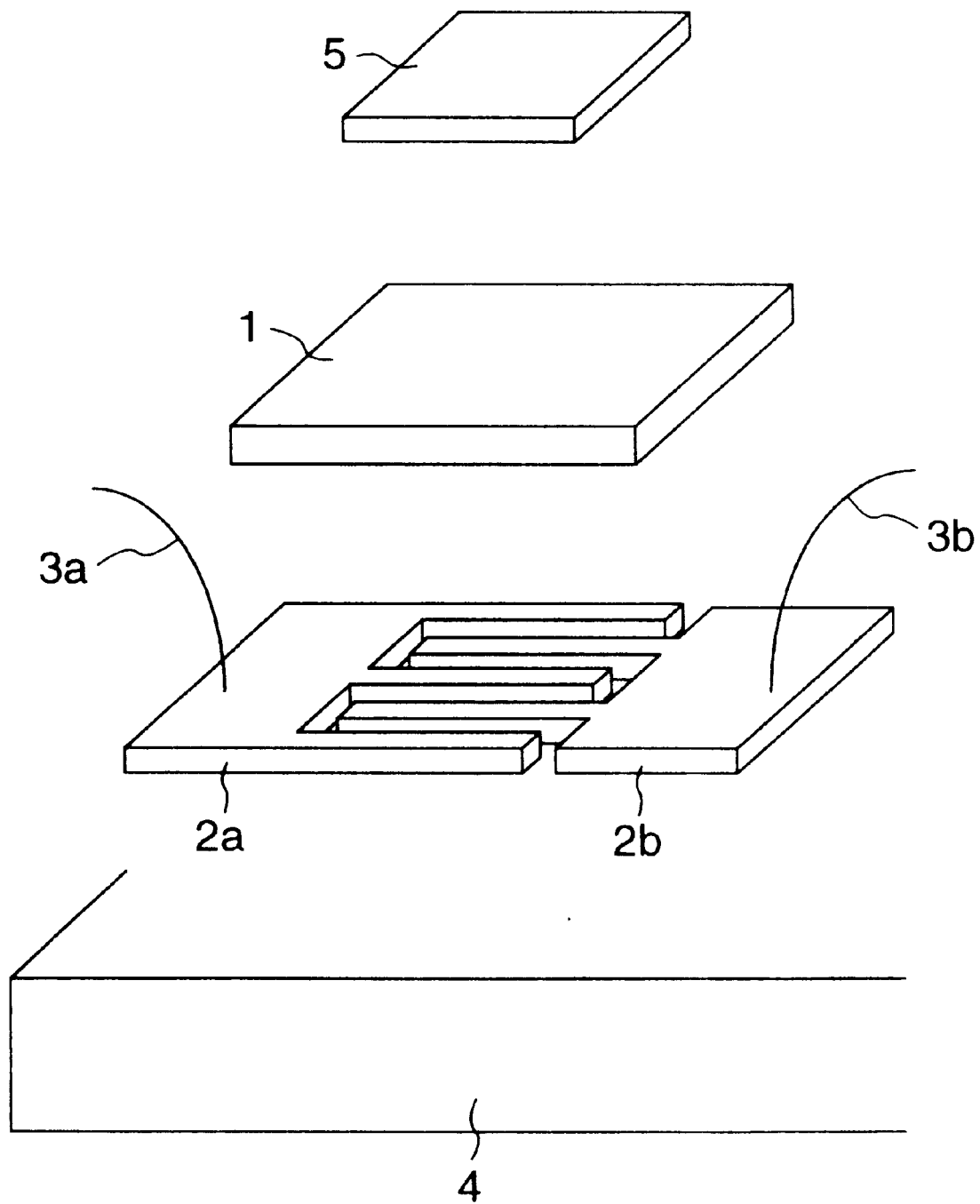
FIG. 3 is an exploded perspective view of the principal part of the carbon dioxide gas sensor in the third embodiment of the present invention.

FIG. 2 is a sectional view of a carbon dioxide gas sensor in the second embodiment of the present invention, and FIG. 3 is an exploded perspective view of the principal part of the carbon dioxide gas sensor in the third embodiment of the present invention.

The carbon dioxide gas sensor in the second embodiment comprises an insulating substrate 4 of alumina or the like, electricity-conducting electrodes 2a and 2b provided on the insulating substrate 4, lead wires 3a and 3b provided on the electricity-conducting electrodes 2a and 2b, a carbon dioxide gas detection part 1 provided on or above the insulating substrate 4 so as to come in contact with the electricity-conducting electrodes 2a and 2b, a counter electrode 5 provided on the carbon dioxide gas detection part 1, electrodes for heating means, 2c and 2d, provided on the insulating substrate 4, lead wires 3c and 3d provided on the electrodes for heating means 2c and 2d, and a heating means 6 provided on the insulating substrate 4 so as to come in contact with the electricity-conducting electrodes 2c and 2d. The sensor may further comprise protective layers 7a and 7b formed on the carbon dioxide gas detection part 1, on the counter electrode 5 and on the heating means 6, providing that the protective layer 7a on the carbon dioxide gas detection part 1 must be provided with a portion which contacts with the outside gas, to make the carbon dioxide gas detection possible.

The carbon dioxide gas sensor in the second embodiment differs from that of the first embodiment in that the former comprises a counter electrode 5 provided on a surface that is opposite to the surface on which the electricity-conducting electrodes 2a and 2b are provided, together with the electricity-conducting electrodes 2a and 2b provided on the carbon dioxide gas detection part 1. The role of the counter electrode 5 is to facilitate the conduction of electricity by passing electricity from the electricity-conducting electrode 2a to the counter electrode 5 and further from the counter electrode 5 to the electricity-conducting electrode 2b. However, the sensor of the present invention can function without being provided with the counter electrode 5.

The carbon dioxide gas detection part 1 used in the present embodiment may be either a sintered body obtained by the process for producing a carbon dioxide gas sensor according to the first embodiment to the third embodiment or it may be a screen-printed film or plated film using the starting material powder shown in the third process for production.

The heating means 6 may be formed, for example, by screen printing a paste containing Pt or $RuO_2$, followed by heat treatment. The electrodes for heating means, 2c and 2d, and the counter electrode 5 may be prepared, like the electricity-conducting electrodes 2a and 2b, for example by screen printing a paste containing any of Au, Pt, Ag, $RuO_2$, or the like, followed by heat treatment. As the lead wires 3c and 3d, there may be used, as in the lead wires 3a and 3b, Pt, Ni, Au or the like in the form of plate or wire. As the protective layers 7a and 7b, there may be used heat resisting glass or the like.

The electricity-conducting electrodes 2a and 2b in the carbon dioxide gas sensor of the present embodiment may be in the form of rectangle and be provided to face each other, or they may be comblike and be provided opposite to each other as shown in FIG. 3 of the third embodiment of the present invention. However, the sensor must be constructed such that part of the electricity-conducting electrodes 2a and 2b overlap the counter electrode 5 via the carbon dioxide gas detection part 1.

The carbon dioxide gas sensor having the above-mentioned structure is used for detecting carbon dioxide gas concentration in a conventional manner. Thus, a predetermined voltage is applied between the lead wires 3c and 3d to make the heating means 6 generate heat, and the carbon dioxide gas detection part 1 is heated to a predetermined temperature; in this state, while passing a sample gas of which the carbon dioxide gas concentration is to be determined, such electric property as impedance or capacitance between the lead wires 3a and 3b is measured to detect the carbon dioxide gas concentration. The impedance phase angle θ at the time of operation falls in the range defined by $-50° \leq \theta \leq -3°$ The heating means shown in the present embodiment may be provided on the insulating substrate either on the same side as the electricity-conducting electrode or on the opposite side.

The insulating substrate used in the carbon dioxide gas sensor of the present embodiment must have at least an insulating surface, have a high mechanical strength and be resistant to the heat treatment temperature at the time of preparation and to the operating temperature. It may be, for example, an electroconductive substrate having an insulating film formed on its surface. In order to improve the heat efficiency of the integral type carbon dioxide gas sensor in which the carbon dioxide gas detection part 1 and the heating means 6 are provided on the same substrate, an insulating material with a good heat conductivity may be provided between the insulating substrate and the carbon dioxide gas detection part 1 and between the insulating substrate and the heating means 6 so that the heat of the heating means 6 may be readily conducted to the carbon dioxide gas detection part 1.

According to the carbon dioxide gas sensor of the present embodiment constructed as described above, a carbon dioxide gas sensor can be provided which has a high detection sensitivity to carbon dioxide gas concentration, high detection speed and high reliability. Furthermore, since the carbon dioxide gas detection part 1 and the heating means 6 can be integrated in one body, the sensor does not need an external heating means and hence can be made in a smaller size.

The process for production according to the present invention is described below.

In the first process for production, first at least one carbonate and at least one carbonate decomposition catalyst, preferably at least one carbonate, at least one carbonate decomposition catalyst and at least one semiconductor oxide are mixed using solvent such as ethanol as the dispersion medium.

The mixture obtained above is fired at 400– 1,000° C., then ground by using the dispersion medium, and the dispersion medium is removed by drying. To the resulting powder mixture is added a sol containing silica as the main component so as to give a solid content of the resulting mixture of 1–15% by weight, then the mixture is kneaded and made into particles. The particles are shaped into the formed article with pressing and then fired at about 550–900° C. to obtain a sintered body. The sol preferably further contains a salt or a complex which comprises the metal component of the carbon dioxide gas detection part.

The sintered body obtained above is used as the carbon dioxide gas detection part. Onto the both sides of the carbon dioxide gas detection part is coated as electrodes a commercially available platinum paste in the form of circle. Then platinum wires are stuck to the coated parts as lead wires, and the resulting system is heat-treated. The electrode may also be formed by screen printing a paste containing another noble metal, such as Au and Ag, or an electroconductive oxide, such as $RuO_2$. In particular, platinum and $RuO_2$ are preferable since platinum and $RuO_2$ show a high adhesive strength with the carbon dioxide gas detection part and are quite effective in resisting to swelling of the carbon dioxide gas detection part caused by moisture absorption.

As the second process for production, whereas in the above-mentioned process the pressed body is prepared after mixing a sol containing silica as the main component as a means for increasing the mechanical strength of the carbon dioxide gas detection part, a process may be adopted in which a sintered body is formed by using a powder mixture of starting materials alone, then the body is dipped in the above-mentioned sol, taken up from the sol, dried and heat treated. In detail, at least one carbonate and at least one carbonate decomposition catalyst, preferably at least one carbonate, at least one carbonate decomposition catalyst and at least one semiconductor oxide are mixed using solvent such as ethanol as a dispersion medium. The resulting mixture is fired at 400–1,000° C., then ground by using the dispersion medium, thereafter dried to remove the dispersion medium and made into particles. The particles are shaped into the formed article with pressing and then fired at about 550–900° C. to obtain a sintered body. The sintered body is dipped in a sol containing colloidal particles of silica as the main component. The system is subjected to an evacuation treatment in order that the sol may permeate completely into the sintered body. Then the sintered body is taken up from the sol and dried to effect gelation of the colloidal particles and obtain a carbon dioxide gas detection part. To the both sides of the carbon dioxide gas detection part is coated such as a Pt paste to serve as electrodes, then lead wires are attached to the electrodes, and the resulting system is baked to obtain a carbon dioxide gas sensor. The dipping step using the sol may be omitted.

The third process for production is described below as the third embodiment of the present invention.

First, as the mixing and dissolving step, acetic acid salts of the metal component of the carbon dioxide gas detection part are mixed and dissolved in a solvent.

Then, as the drying step, the acetic acid salts solution obtained in the mixing and dissolving step is heated while being stirred to evaporate off the solvent, to obtain a powder mixture.

Then, as the heat decomposition step, the powder mixture obtained in the drying step is heated to effect heat decomposition. It is estimated that the respective components in the powder mixture are converted into oxides and carbonates by the heat decomposition. In the heat decomposition step, if necessary and desired, the heat treatment is conducted in an atmosphere containing carbon dioxide gas to promote carbonization. The average particle diameter of the powder mixture heat-decomposed falls in the range of 0.05 $\mu$m–0.6 $\mu$m, preferably 0.1 $\mu$m–0.5 $\mu$m.

The powder mixture obtained in the heat decomposition step may be heat-treated as the calcination step at a higher temperature than in the heat treatment of the heat decomposition step to promote the calcining of the powder mixture and the growth of grains. The heat decomposition step or the calcination step yields a powder mixture comprises at least a carbonate and a carbonate decomposition catalyst, preferably at least a carbonate, a carbonate decomposition catalyst and a semiconductor oxide.

Then, as the shaping step, the powder mixture is ground and then shaped into a formed article.

Then, as the firing step, the formed article obtained in the shaping step is sintered by heating, to obtain the detection part of a carbon dioxide gas sensor.

A carbon dioxide detection part also may be obtained by using a paste comprising the powder mixture obtained in the heat decomposition step. The paste is coated on an insulating substrate to form a film for example by screen printing. The film obtained serves as a carbon dioxide detection part.

Then, on the carbon dioxide detection part thus obtained are formed by conventional methods at least two electricity-conducting electrodes, whereby a carbon dioxide gas sensor is obtained.

Thus, according to the present embodiment of the invention, a starting material powder for preparing a carbon dioxide gas detection part with an excellent moisture resistance and a high carbon dioxide gas detection speed can be provided.

Furthermore, by shaping and firing the above-mentioned starting material powder, a carbon dioxide gas detection part with a high carbon dioxide gas detection sensitivity and high detection speed can be prepared in a simple way, and a carbon dioxide gas sensor with a high and stable quality can be mass-produced at a low cost.

The process for producing a carbon dioxide gas sensor according to the present embodiment of the invention may also comprise the step of providing a carbon dioxide gas detection part on an insulating substrate, such as alumina substrate, and forming an electrode on the carbon dioxide gas detection part.

Furthermore, the process may further comprise the step of providing on such an insulating substrate a heating means for heating the carbon dioxide gas detection part to a predetermined temperature and the step of forming a heat resisting protective layer of glass or the like on the electricity-conducting electrode, lead wire, carbon dioxide gas detection part and heating means. In the case of forming a heat resisting protective layer on the carbon dioxide gas detection part, the layer should be formed such that a part of the carbon dioxide gas detection part is exposed to the outside to enable the contact of carbon dioxide gas with the carbon dioxide detection part.

In forming the carbon dioxide gas detection part on the insulating substrate by using the starting material powder according to the present embodiment, there may also be used screen printing, electroplating and physical vapor deposition, such as sputtering, without impairing the effect of the present invention.

The methods for evaluating the carbon dioxide gas sensor obtained by the above-mentioned production process are described below.

The method used for detecting carbon dioxide gas concentration by using the carbon dioxide gas sensor having the aforesaid structure is the same as in the prior art methods. For example, the carbon dioxide gas sensor in the present embodiment is placed in an electric furnace or other external heating means and, while a sample gas of which the carbon dioxide concentration is to be determined is being passed, such electric property as impedance or capacitance between the lead wires 3a and 3b is measured, to detect the carbon dioxide gas concentration.

A test for detection sensitivity to carbon dioxide concentration as described below was conducted.

Each of the carbon dioxide gas sensors to be tested was placed in an electric furnace controlled at 550° C., and the capacitive component of impedance between lead wires at a frequency of 50 kHz was determined by the two terminal network method and by applying an alternating voltage of 0.5 V to the carbon dioxide gas sensor by using an impedance analyzer (4192A, mfd. by YHP Corp.) under a condition of passing dry air into the electric furnace and under a condition of passing dry air containing 2% of carbon dioxide into the furnace. The capacitive component of impedance was measured until an approximately constant value is reacted while dry air or dry air containing carbon dioxide of a concentration of 2% was being passed into the electric furnace, and the constant value was taken as the capacitive component of impedance.

From the capacitive component of impedance measured under a condition of passing dry air in the electric furnace, C1, and the capacitive component of impedance measured under a condition of passing dry air containing carbon dioxide of a concentration of 2%, C2, the detection sensitivity to carbon dioxide gas is determined according to the following equation:

$$detection\ sensitivity\ (dB) = |10 * log(C2/C1)|.$$

It can be said from the above equation that the larger the value of detection sensitivity, the better the detection sensitivity to carbon dioxide gas. The time necessary for the value of the capacitive component of impedance to reach 90% of the ultimate constant value from the beginning of passing dry air or carbon dioxide-containing dry air into the electric furnace is termed "90% detection time", which is determined for each individual carbon dioxide gas sensor.

The life test is conducted by determining the detection sensitivity to carbon dioxide gas after allowing a carbon dioxide gas sensor to stand in an electric furnace maintained at 550° C. for 10,000 hours.

The high-temperature high-humidity test of a carbon dioxide gas sensor is described below. First, a carbon dioxide gas sensor is kept at a temperature of 550° C. and the impedance for a carbon dioxide gas concentration of 2% is determined. The value obtained by the determination is taken as "the detection sensitivity before test" and is denoted as $S_1(dB)$. As the high-temperature high-humidity test, the carbon dioxide gas sensor is allowed to stand in a constant temperature and humidity chamber of 85° C. and 90% RH for 1,000 hours. During the time the electric source for the carbon dioxide gas sensor is turned off and the carbon dioxide gas detection part is not heated. Thereafter the sensor is kept at a temperature of 550° C. and the impedance for a carbon dioxide gas concentration of 2% is determined. The value thus determined is taken as "the detection sensitivity after test", $S_2(dB)$.

By using the detection sensitivity before test, $S_1(dB)$, and the detection sensitivity after test, $S_2(dB)$, $\Delta S$ is defined by the following equation:

$$\Delta S = (S_1 - S_2)/S_1 \times 100(\%).$$

The high-temperature high-humidity characteristic of the sensor is evaluated by the value of $\Delta S$ (%).

EXAMPLE 1

First, a sample sensor was prepared according to the first production process by using barium carbonate ($BaCO_3$) powder, cerium oxide ($CeO_2$) powder and copper oxide (CuO) powder (each mfd. by Wako Pure Chemical Industries, Ltd.).

Thus, barium carbonate ($BaCO_3$) powder, cerium oxide ($CeO_2$) powder and copper oxide (CuO) powder were weighed in a molar ratio of 6:63:31 and mixed in a ball mill using ethanol as the dispersion medium for 45 hours.

The mixture obtained was fired in the air at 700° C. for 5 hours, then ball-milled again by using ethanol for 45 hours and dried to remove the ethanol. To the resulting powder mixture was added a sol containing silica and ceria, and the mixture was kneaded and then made into particles of predetermined size by using mesh. The particles were shaped into the form of disk 10 mm in diameter and 0.4 mm in thickness with a pressing machine at a pressure of 30 kg/cm², and then fired at 900° C. for 5 hours to obtain a sintered body.

The sintered body obtained above was used as the carbon dioxide gas detection part. Onto the both sides of the carbon dioxide gas detection part was coated as electrodes a commercially available platinum paste in the form of circle. Then platinum wires were stuck to the coated parts as lead wires, and the resulting system was heat-treated at 800° C. for 10 minutes.

According to the X-ray diffraction, FT-IR, and TG analysis, the carbon dioxide gas detection part was a mixture consisting essentially of $BaCO_3$, BaO, $BaO_2$, $CeO2$ and CuO.

The sample sensor thus obtained was evaluated for its detection sensitivity to carbon dioxide gas concentration and its moisture resistance characteristic by using the methods described before.

Sample sensors using another mixture of a carbonate, a carbonate decomposition catalyst and a semiconductor oxide shown in Tables 1–3 were prepared and similar results to those of the present Example were obtained. The values of ΔS (%) obtained in the investigation are shown in Tables 1–3.

TABLE 1

|    | Group A | Group B | Group C | ΔS (%) |
|----|---------|---------|---------|--------|
| 1  | $BaCO_3$ | $CeO_2$ | CuO | 5 |
| 2  | $BaCO_3$ | $CeO_2$ | Pbo | 8 |
| 3  | $BaCO_3$ | $CeO_2$ | FeO | 9 |
| 4  | $BaCO_3$ | $CeO_2$ | ZnO | 15 |
| 5  | $BaCO_3$ | $CeO_2$ | SnO | 14 |
| 6  | $BaCO_3$ | $CeO_2$ | 50% CuO + 50% PbO | 7 |
| 7  | $BaCO_3$ | $BaTiO_3$ | CuO | 9 |
| 8  | $BaCO_3$ | $SrTiO_3$ | CuO | 13 |
| 9  | $BaCO_3$ | $CaTiO_3$ | CuO | 13 |
| 10 | $BaCO_3$ | $BaCeO_3$ | CuO | 21 |

TABLE 2

|    | Group A | Group B | Group C | ΔS (%) |
|----|---------|---------|---------|--------|
| 11 | $BaCO_3$ | $SrCeO_2$ | CuO | 18 |
| 12 | $BaCO_3$ | $CeO_2$ | CuO | 10 |
| 13 | $SrCO_3$ | $CeO_2$ | PbO | 9 |
| 14 | 50% $BaCO_3$ + 50% $CaCO_3$ | $CeO_2$ | Pbo | 10 |
| 15 | 50% $BaCO_3$ + 50% $SrCO_3$ | $CeO_2$ | PbO | 11 |
| 16 | 50% $BaCO_3$ + 50% $SrCO_3$ | $BaTiO_3$ | PbO | 11 |
| 17 | $SrCO_3$ | $Y_2O_3$ | ZnO | 14 |
| 18 | $SrCO_3$ | $Gd_2O_3$ | ZnO | 18 |
| 19 | $SrCO_3$ | $Ld_2O_3$ | ZnO | 17 |
| 20 | $CaCO_3$ | $Sc_2O_3$ | ZnO | 19 |

TABLE 3

|    | Group A | Group B | Group C | ΔS (%) |
|----|---------|---------|---------|--------|
| 21 | $SrCO_3$ | 10% $BaTiO_3$ + 90% $SrTiO_3$ | ZnO | 21 |
| 22 | $SrCO_3$ | 30% $BaTiO_3$ + 70% $BaCeO_2$ | ZnO | 19 |
| 23 | $BaCO_3$ | 40% $SrTiO_3$ + 60% $SrCeO_2$ | FeO | 16 |
| 24 | $BaCO_3$ | 20% $BaTiO_3$ + 80% $CeO_2$ | FeO | 16 |
| 25 | $CaCO_3$ | 15% $BaTiO_3$ + 85% $CeO_2$ | FeO | 17 |
| 26 | $CaCO_3$ | 25% $SrTiO_3$ + 75% $CeO_2$ | FeO | 17 |
| 27 | $BaCO_3$ | 80% $CeO_2$ + 20% $Gd_2O_3$ | FeO | 15 |
| 28 | $BaCO_3$ | 80% $CeO_2$ + 20% $Y_2O_3$ | FeO | 16 |
| 29 | 50% $BaCO_3$ + 50% $CaCO_3$ | 25% $SrTiO_3$ + 75% $CeO_2$ | SnO | 19 |
| 30 | 50% $BaCO_3$ + 50% $SrCO_3$ | 80% $CeO_2$ + 20% $Gd_2O_3$ | SnO | 26 |
| 31 | 50% $BaCO_3$ + 50% $SrCO_3$ | 80% $CeO_2$ + 20% $Y_2O_3$ | SnO | 22 |
| 32 | 90% $BaCO_3$ + 10% $Li_2CO_3$ | $CeO_2$ | CuO | 29 |

According to a thermogravimetric analysis, it was found that the materials of the group B shown in Tables 1–3 exert a catalytic action of decomposing the carbonates of the group A at a low temperature. Thus, when a mixture of an oxide of the group B and a carbonate of the group A was heated in air the mixture decreased its weight and, when carbon dioxide gas was introduced the mixture reversibly increased its weight. Further, the X-ray diffraction and FT-IR analysis of the mixture which had decreased its weight revealed that the reversible decrease and increase of weight were caused by the decomposition and formation of carbonate. Although similar decomposition-formation reaction takes place also in a material of the group A alone when the material is brought to a high temperature, a mixed system of the group A and the group B underwent a decomposition-formation reaction of carbonate at a temperature lower by 200° C. than in the case of the group A alone. It can be judged, from the foregoing, that the oxide of the group B has a catalytic function of decomposing the carbonate of the group A at a low temperature.

The low-temperature catalytic function of the carbonate decomposition catalyst of the group B is of great importance in detecting carbon dioxide gas. Prior art devices prepared from a mixture of the group A and the group C which does not contain the group B has a very low detection sensitivity to carbon dioxide gas. For example, when barium carbonate ($BaCO_3$) was used as the carbonate selected from the group A and copper oxide (CuO) as the semiconductor oxide selected from the group C, the mixture gave a detection sensitivity of 0.1 dB or less in whatever composition ratio it was made.

Furthermore, $BaCO_3$, which, though it is the most excellent in moisture resistance among alkali metal carbonates and alkaline earth metal carbonates, shows a temperature of undergoing decomposition to evolve carbon dioxide gas of as high as about 1200° C. and hence has been difficult to use as a detecting material in the prior art, can be used as a detecting material in the present invention. In this respect, the novel technique of adding a carbonate decomposition catalyst of the group B of the present invention is of great significance.

The semiconductor oxide of the group C has a function of converting the decomposition-formation reaction of carbonate in the sintered body of a mixture of the group A and the group B to an electric signal and amplifying the signal. For example, though a sintered body of the group A and the group B alone shows change in impedance with carbon dioxide gas concentration, the amount of change is becomes bigger to which the group C has been added.

Thus, the essential point of the present invention lies in that the carbon dioxide gas detection part is prepared from a mixture containing at least one carbonate and at least one carbonate decomposition catalyst, preferably at least one carbonate, at least one carbnate decomposition catalyst and at least one semiconductor oxide and that the carbon dioxide gas detection part comprises at least one carbonate and at least one carbonate decomposition catalyst, preferably at least one carbonate, at least one carbonate decomposition catalyst and at least one semiconductor oxide.

Though the respective functions of the materials of the groups A, B and C were described above, an additional important condition desirable for the materials when they are mixed into a mixed system is that in the mixed system the constituents should be inert to one another, in other words, they should be difficultly sinterable. When the reactivity of the constituents is high, the detection sensitivity may decrease or the sensitivity may change greatly with the passage of time depending on particular sintering conditions. In consideration of the difficult sinterability and moisture resistance, it is preferable to select barium carbonate ($BaCO_3$) as the carbonate of the group A and cerium oxide ($CeO_2$) as the carbonate decomposition catalyst of the group B. The material of the semiconductor oxide of the group C needs not be particularly selected, and any of those shown in Tables 1–3 may be used.

EXAMPLE 2

Sensor samples were prepared by varying the mixing ratio of barium carbonate ($BaCO_3$), cerium oxide ($CeO_2$) and copper oxide (CuO).

Specifically, first, $BaCO_3$ powder, $CeO_2$ powder and CuO powder (each mfd. by Wako Pure Chemical Industries, Ltd.) were mixed in proportions shown in Tables 4 and 5.

TABLE 4

| | Composition (mol %) | | | Sintering temperature | Measuring temperature | Phase angle | $R_0$ | $R_{300}$ |
|---|---|---|---|---|---|---|---|---|
| | X | Y | Z | (° C.) | (° C.) | (deg) | (dB) | (dB) |
| Sample 1 | 3 | 65 | 32 | 800 | 550 | −24 | 6.1 | 6.0 |
| Sample 2 | 3 | 63 | 34 | 800 | 550 | −19 | 6.5 | 6.4 |
| Sample 3 | 6 | 63 | 31 | 800 | 550 | −8 | 7.1 | 7.1 |
| Sample 4 | 9 | 63 | 28 | 800 | 550 | −11 | 7.2 | 6.9 |
| Sample 5 | 12 | 63 | 25 | 800 | 550 | −17 | 6.9 | 6.4 |
| Sample 6 | 15 | 60 | 25 | 800 | 550 | −38 | 5.5 | 5.5 |
| Sample 7 | 15 | 55 | 30 | 800 | 550 | −47 | 5.3 | 5.3 |
| Sample 8 | 15 | 50 | 35 | 800 | 550 | −47 | 5.4 | 5.3 |
| Sample 9 | 15 | 45 | 40 | 800 | 550 | −5 | 6.6 | 6.3 |
| Sample 10 | 15 | 40 | 45 | 800 | 550 | −3 | 6.9 | 6.4 |
| Sample 11 | 20 | 80 | 0 | 950 | 650 | −42 | 5.6 | 5.6 |
| Sample 12 | 30 | 70 | 0 | 950 | 650 | −45 | 5.5 | 5.3 |

TABLE 5

| | Composition (mol %) | | | Sintering temperature | Measuring temperature | Phase angle | $R_0$ | $R_{300}$ |
|---|---|---|---|---|---|---|---|---|
| | X | Y | Z | (° C.) | (° C.) | (deg) | (dB) | (dB) |
| Sample 13 | 40 | 60 | 0 | 950 | 650 | −41 | 5.1 | 5.0 |
| Sample 14 | 50 | 50 | 0 | 950 | 650 | −36 | 5.8 | 5.6 |
| Sample 15 | 40 | 50 | 10 | 950 | 650 | −27 | 6.1 | 5.7 |
| Sample 16 | 40 | 40 | 20 | 950 | 650 | −15 | 8.7 | 8.5 |
| Sample 17 | 40 | 30 | 30 | 950 | 650 | −19 | 7.1 | 7.0 |
| Sample 18 | 40 | 20 | 40 | 950 | 650 | −47 | 5.2 | 5.2 |
| Sample 19 | 30 | 60 | 10 | 950 | 650 | −39 | 5.5 | 5.1 |
| Sample 20 | 30 | 50 | 20 | 950 | 650 | −45 | 5.6 | 5.1 |
| Sample 21 | 30 | 40 | 30 | 950 | 650 | −41 | 5.3 | 5.3 |
| Sample 22 | 30 | 30 | 40 | 950 | 650 | −48 | 5.1 | 5.1 |
| Comparative Sample 1 | 0 | 100 | 0 | 800 | 550 | −76 | 0 | — |
| Comparative Sample 2 | 0 | 70 | 30 | 800 | 550 | −65 | 1.2 | — |

To the resulting powder mixture was added ethanol as the dispersant and they were uniformly mixed in a ball mill for 45 hours. The mixture obtained was fired in the air at 800° C. and 950° C. for 5 hours. The fired product was mixed with ethanol and ground into powder in a ball mill for 45 hours, then ethanol was removed by drying, and the remaining powder was made into a predetermined size by using mesh. The powder thus obtained was shaped into the form of disk 10 mm in diameter and 0.4 mm in thickness by pressing with a pressing machine at a pressure of 30 kg/cm² and then fired at 900° C. for 5 hours to obtain a sintered body.

With the sintered body obtained above used as a carbon dioxide gas detection part, a commercially available platinum paste was coated in the form of circle as electrodes onto the both sides of the carbon dioxide gas detection part. Then platinum wires were stuck as lead wires to the coated parts, and the resulting system was heat-treated at 800° C. for 10 minutes.

Thus, carbon dioxide gas sensors of sample 1 to sample 22 were prepared.

Separately, comparative samples 1 and 2 were prepared for comparison. Comparative sample 1 contains neither the material of group A nor the material of group C. Comparative sample 2 contains no material of group A. The method of preparation for these comparative samples 1 and 2 were the same as in the preparation of samples 1–22. Their composition ratios are shown in Table 5.

Sample A was prepared as follows.

$BaCO_3$ powder (mfd. by Wako Pure Chemical Industries, Ltd.) and $TiO_3$ powder (mfd. by Nippon Aerosil Co.) were mixed in an equimolar ratio and fired in the air at 1200° C. for 12 hours to obtain $BaTiO_3$ powder. Then, $BaCO_3$ powder (mfd. by Wako Pure Chemical Industries, Ltd.), $BaTiO_3$ powder obtained above and CuO powder (mfd. by Wako Pure Chemical Industries, Ltd.) were mixed in a molar ratio of 1:49:50, and fired at 800° C. for 5 hours. Subsequent preparation steps were the same as those for samples 1–22.

The detection sensitivity to carbon dioxide gas of samples 1–22 and comparative samples 1 and 2 were determined. The method of determination was the same as described above. The change of detection sensitivity with the passage of time was also determined. The detection sensitivity at the time of initiation of determination was designated as $R_0$ and the detection sensitivity 300 days after initiation of determination was designated as $R_{300}$. The phase angles of impedance, $R_0$ and $R_{300}$ obtained in the determination with samples 1–22 and comparative samples 1 and 2 are shown in Tables 4 and 5.

Tables 4 and 5 reveal the following. In the samples of the present invention of Example 2 the detection sensitivities were 5 dB or more; particularly, sample 16 showed a very high detection sensitivity of 8.7 dB. The phase angles of impedance of samples 1–22 were in the range of from −48° to −3°. The detection sensitivities of comparative samples 1 and 2 were as low as 0 and 1.2 dB, respectively, and the phase angles of impedance of them were −76° and −65°, respectively. Furthermore, the samples according to the present invention showed a very little decrease in detection sensitivity of 0–0.5 dB even after the lapse of 300 days and thus underwent little deterioration with the passage of time.

Figure 4:
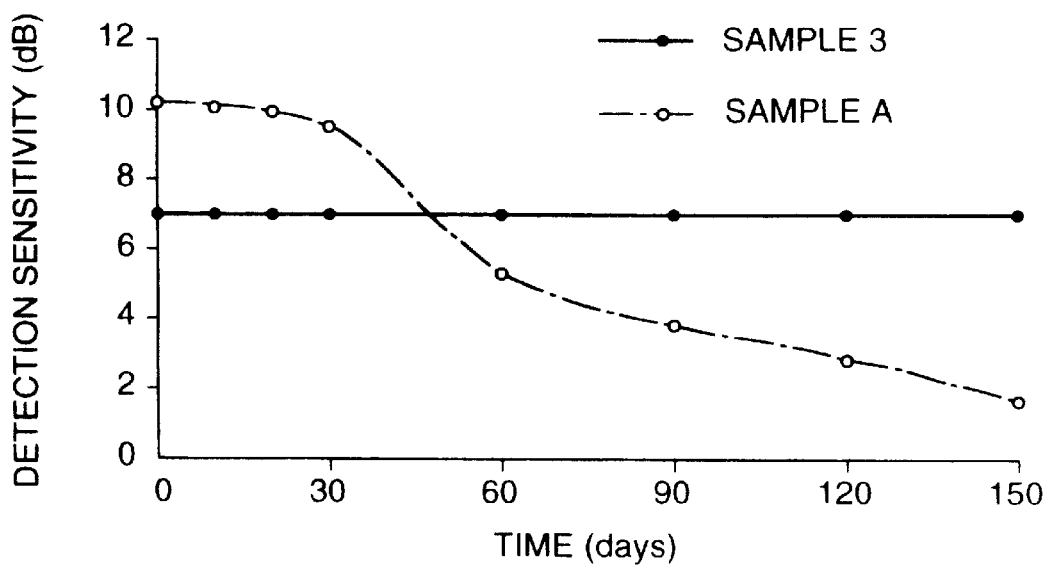
FIG. 4 is a graph showing the relation between the passage of time and the detection sensitivity in Sample 3 and Sample A.
Figure 5:
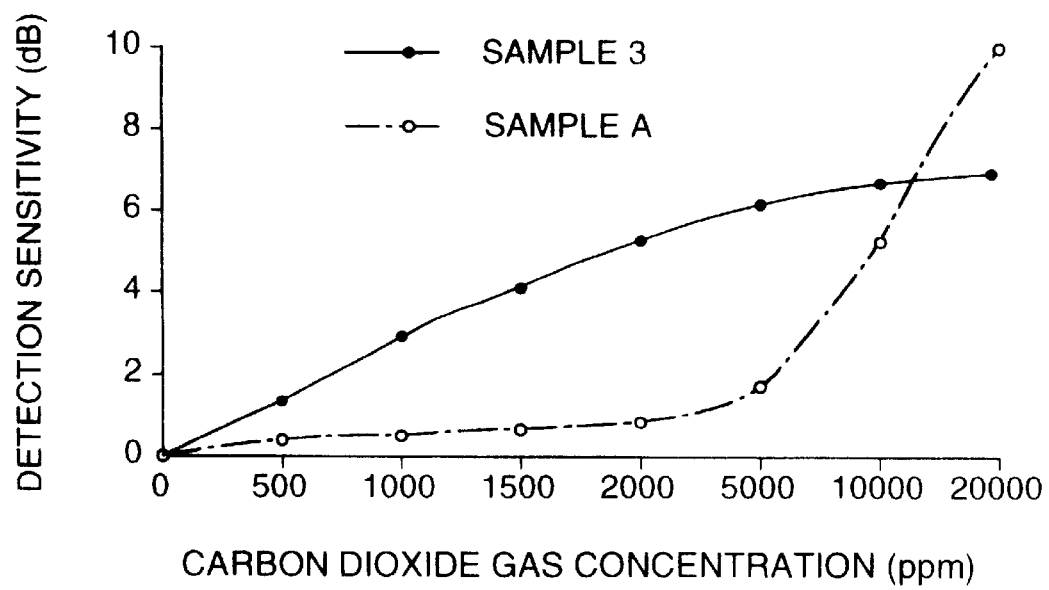
FIG. 5 is a graph showing the relation between the carbon dioxide gas concentration and the detection sensitivity in Sample 3 and Sample A.

Subsequently, the change of detection sensitivity with the passage of time and the dependency of detection sensitivity on carbon dioxide gas concentration were determined with sample 3 and sample A. The methods of determination were the same as described before. FIG. 4 is a graph showing the relation between the detection sensitivity and the passage of time for sample 3 and sample A. FIG. 5 is a graph showing the relation between the detection sensitivity and the carbon dioxide gas concentration for the same samples.

FIGS. 4 and 5 revealed the following. In sample 3 according to the present invention, the detection sensitivity decreased by only 0.5% in standing for 60 days and only 1% in standing 150 days; thus the change of sensitivity with the passage of time was very small. In sample 3, further, the detection sensitivity increased gradually in the range of 2–6 dB are the carbon dioxide gas concentration increased in the range of 500–5,000 ppm, showing a high detection sensitivity to carbon dioxide gas and a high rate of change of the sensitivity with the carbon dioxide gas concentration.

EXAMPLE 3

Commercially available barium acetate ($Ba(CH_3COO)_2$), cerium acetate ($Ce(CH_3COO)_3 \cdot H_2O$) and copper acetate (Cu(CH$_3$COO)$_2$.H$_2$O) were weighed so as to give a molar ratio of the metal components of 20:45:35 and a total amount of 500 g, and all the acetate were dissolved in 5 l of pure water.

The acetate solution obtained was heated while being stirred by using a hot stirrer to effect drying. The powder mixture thus obtained was transferred into a heat treating vessel and heat-decomposed by heating in an electric furnace at 300° C. for 2 hours. It may be further subjected to a carbonization treatment in a stream of gas mixture consisting of dry air and 10% of carbon dioxide at 500° C. for 5 hours.

Then, the heat-decomposed powder mixture obtained above was ground in a mortar, and the ground product was shaped into a disk 10 mm in diameter and 0.4 mm in thickness and fired in an electric furnace at 800° C. for 5 hours to obtain a sintered body.

With the sintered body obtained above used as a carbon dioxide gas detection part, a commercially available platinum paste was coated in the form of circle as electrodes onto the both sides of the carbon dioxide gas detection part. Then platinum wires were stuck as lead wires to the coated parts, and the resulting system was heat-treated at 800° C. for 10 minutes.

Thus a carbon dioxide gas sensor of sample 24 was prepared.

Separately, a disk 10 mm in diameter and 0.4 mm in thickness was prepared in the same manner as above, and the disk was fired in an electric furnace at 900° C. for 5 hours to obtain a sintered body. The sintered body was then provided with electrodes and lead wires in the same manner as in Example 1.

Thus a carbon dioxide gas sensor of sample 25 was prepared.

It is estimated that the cerium acetate and the copper acetate used in sample 24 and sample 25 were converted by heat treatment to their respective oxides, and the barium acetate was converted by heat treatment to barium oxide and barium carbonate.

For reference, the following sensor was prepared.

Commercially available barium carbonate, cerium oxide and copper oxide were weighed to give a molar ratio of 20:45:35 and a total amount of 500 g, and mixed and ground in a ball mill for 46 hours. The ground product was shaped into a disk 10 mm in diameter and 0.4 mm in thickness by using a pressing machine, and the disk was fired in an electric furnace at 800° C. for 5 hours to obtain a sintered body.

With the sintered body obtained above used as a carbon dioxide gas detection part, a commercially available platinum paste was coated in the form of circle as electrodes onto the both sides of the carbon dioxide gas detection part, then platinum wires were stuck as lead wires to the coated parts, and the resulting system was heat-treated at 800° C. for 10 minutes.

Thus a carbon dioxide gas sensor of sample B was prepared.

Separately, a disk 10 mm in diameter and 0.4 mm in thickness was shaped in the same manner as in comparative sample 4, and fired in an electric furnace at 900° C. for 5 hours to obtain a sintered body. The sintered body was then provided with electrodes and lead wires in the same manner as in sample B.

Thus a carbon dioxide gas sensor of sample C as prepared.

For comparing the performances of the carbon dioxide gas sensors of samples 24 and 25 and samples B and C, the detection sensitivity to carbon dioxide gas concentration and the 90% detection time described before were determined with respective sample sensors. The results obtained are shown in Table 6.

TABLE 6

|  | Detection sensitivity (dB) | 90% Detection time (min) | Detection sensitivity decrease (%) |
| --- | --- | --- | --- |
| Sample 24 | 7.6 | 1 | 4 |
| Sample 25 | 4.6 | 2 | 1 |
| Sample B | 5.9 | 5 | 15 |
| Sample C | 3.8 | 10 | 12 |

From the comparison of the results obtained with samples 24 and 25 and samples B and C, it was revealed that by using a product obtained by heat treating a powder mixture prepared from aqueous acetic acid salt solution, a higher detection sensitivity and a shorter 90% detection time could be obtained than by using oxide and carbonate as the starting materials; and that with respect to the temperature of firing for obtaining a sintered body which is to be a carbon dioxide detection part, a more improved detection sensitivity and a higher detection speed could be obtained by firing at 800° C. than at 900° C.

The life test was conducted by allowing the carbon dioxide gas sensor to stand in an electric furnace kept at 550° C. for 10,000 hours and then determining the detection sensitivity to carbon dioxide gas.

The detection sensitivities thus obtained are also shown in Table 6.

Resultantly, it was revealed that whereas the carbon dioxide gas sensor of samples B and C showed a decrease of detection sensitivity of 15% and 12%, respectively, as compared with the sensitivity before 10,000 hours of standing, the carbon dioxide gas sensors of samples 24 and 25 showed a very small decrease of detection sensitivity of 4% and 1%, respectively, and thus the carbon dioxide gas sensor prepared from aqueous acetate solution is greatly improved also in durability and life.

Although not shown in Table 6, the impact strength necessary for breaking the carbon dioxide gas sensors of samples 24 and 25 was found to be about 3 times as large as that of samples B and C. This revealed that the carbon dioxide gas sensor prepared from a product obtained by heat treating the powder mixture prepared from aqueous acetate solution is improved in mechanical strength.

The average particle diameters of each of the barium carbonate, cerium oxide and copper oxide contained in the carbon dioxide gas sensors of sample 24 and sample B were determined by using a laser diffraction-scattering particle size distribution analyzer (mfd. by Horiba Seisakusho K.K.).

The average particle diameters thus obtained are summarized in Table 7.

TABLE 7

|  | Average particle diameter ($\mu$m) | | |
| --- | --- | --- | --- |
|  | Barium carbonate | Cerium oxide | Copper oxide |
| Sample 24 | 0.1 | 0.3 | 0.5 |
| Sample B | 0.7 | 3.2 | 3.0 |

Table 7 revealed that the carbon dioxide gas sensor prepared from aqueous acetate solution had a smaller average particle diameter. Further, since the barium component, cerium component and copper component are mixed in the state of aqueous acetate solution, it can be easily estimated that the mixing state of these components is quite excellent as compared with a mixing state obtained by mixing then in powders. When a carbon dioxide gas detection part is prepared by sintering, the smaller the particle diameter of oxides and carbonates of the starting materials are and the more thoroughly they are mixed, the resulting detection part has the higher detection sensitivity and the higher detection speed. It can be considered that such small average particle diameters of the starting material particles and resultant large contact area with carbon dioxide gas constitute an important factor contributing to the excellent characteristic properties of the carbon dioxide gas sensor according to the present invention.

It can also be considered that the improved durability and life of the sensor of the present invention can largely be attributed to the improved mechanical strength of the carbon dioxide gas detection part described above, a good mixing state and good adhesion with the electrode.

As described in the foregoing, according to the present invention, a carbon dioxide gas sensor can be provided which is more excellent than prior art sensors in carbon dioxide gas detection sensitivity, detection speed, moisture resistance and long-term characteristics. Moreover, according to the present invention, the reliability of carbon dioxide gas detection can be improved, for example, in monitors for monitoring pollution of the air in living spaces, such as inside a room and inside a vehicle, monitors for air conditioning systems, carbon dioxide gas concentration control in transportation and storage of perishable foods, and monitoring systems in biotechnical facilities.

What is claimed is:

1. A carbon dioxide gas sensor comprising a carbon dioxide gas detection part for detecting carbon dioxide gas concentration and at least one pair of electrodes formed on the carbon dioxide gas detection part, wherein the carbon dioxide gas detection part comprises a carbonate, a carbonate decomposition catalyst, a carbonate decomposition product formed by the carbonate and the carbonate decomposition catalyst, and a semiconductor oxide.

2. The carbon dioxide gas sensor according to claim 1, wherein the semiconductor oxide is at least one member selected from the group consisting of copper oxides, lead oxides, iron oxides, zinc oxides and tin oxides.

3. The carbon dioxide gas sensor according to claim 1, wherein the carbonate is at least one member selected from the group consisting of alkali metal carbonates and alkaline earth metal carbonates, the carbonate decomposition catalyst is at least one member selected from the group consisting of perovskite oxides and rare earth element oxides and the semiconductor oxide is at least one member selected from the group consisting of copper oxides, lead oxides, iron oxides, zinc oxides and tin oxides.

4. The carbon dioxide gas sensor according to claim 3, wherein the carbonate includes $BaCO_3$.

5. The carbon dioxide gas sensor according to claim 3, wherein the carbonate decomposition catalyst includes $CeO_2$.

6. The carbon dioxide gas sensor according to claim 3, wherein the semiconductor oxide includes $CuO$.

7. The carbon dioxide gas sensor according to claim 1, wherein the carbonate is at least one member selected from the group consisting of alkali metal carbonates and alkaline earth metal carbonates.

8. The carbon dioxide gas sensor according to claim 1, wherein the carbonate decomposition catalyst is at least one member selected from the group consisting of perovskite oxides and rare earth element oxides.

9. The carbon dioxide gas sensor according to claim 1, wherein in the molar mixing ratio of the carbonate, the decomposition catalyst and the semiconductor oxide, expressed as the carbonate:the decomposition catalyst:the semiconductor oxide=X:Y:Z wherein X+Y+Z=100, X, Y and Z respectively fall within the range defined by the equation $3 \leq X \leq 50$, $30 \leq Y \leq 80$ and $0 < Z \leq 45$.

10. The carbon dioxide gas sensor according to claim 1, wherein a noble metal or an oxide conductor is used as the electrodes.

11. The carbon dioxide gas sensor according to claim 10, wherein the noble metal is platinum.

12. The carbon dioxide gas sensor according to claim 1, wherein an impedance phase angle θ of the carbon dioxide gas detection part at the time of operation falls in the range defined by $-50° \leq \theta \leq -3°$.

13. The carbon dioxide gas sensor according to claim 1, wherein the carbon oxide gas detection part and a heating means are provided on a same substrate.

14. The carbon dioxide gas sensor according to claim 1, wherein a pair of electricity-conducting electrodes are provided on one side of the carbon dioxide gas detection part and at least one counter electrode is provided on a surface which is opposite to the aforesaid side of the carbon dioxide detection part.

15. The carbon dioxide gas sensor according to claim 1, wherein the carbonate decomposition catalyst is at least one member selected from the group consisting of $CeO_2$, $Y_2O_3$, $Gd_2O_3$, $La_2O_3$, $Sc_2O_3$, $SrTiO_3$, $CaTiO_3$, $BaCeO_3$ and $SrCeO_3$.

16. A carbon dioxide gas sensor comprising a carbon dioxide gas detection part for detecting carbon dioxide gas concentration and at least one pair of electrodes formed on the carbon dioxide gas detection part, wherein the carbon dioxide gas detection part comprises a carbonate, a carbonate decomposition catalyst consisting of $CeO_2$, and a carbonate decomposition product formed by the carbonate and the carbonate decomposition catalyst.

17. The carbon dioxide gas sensor according to claim 16, wherein the carbon dioxide gas detection part further comprises a semiconductor oxide.

18. The carbon dioxide gas sensor according to claim 17, wherein the carbonate is at least one member selected from the group consisting of alkali metal carbonates and alkaline earth metal carbonates and the semiconductor oxide is at least one member selected from the group consisting of copper oxides, lead oxides, iron oxides, zinc oxides and tin oxides.

19. The carbon dioxide gas sensor according to claim 18, wherein the carbonate is $BaCO_3$ and the semiconductor oxide is $CuO$.

20. The carbon dioxide gas sensor according to claim 16, wherein the carbonate is at least one member selected from the group consisting of alkali metal carbonates and alkaline earth metal carbonates.

* * * * *